(12) United States Patent
Slutz et al.

(10) Patent No.: US 8,562,914 B2
(45) Date of Patent: Oct. 22, 2013

(54) DEODORIZING SYSTEM AND METHOD FOR USE THEREOF

(75) Inventors: John D. Slutz, East Sparta, OH (US); Jack L. Stimmel, Canton, OH (US)

(73) Assignee: JMW Welding & Manufacturing, Inc., Canton, OH (US)

( * ) Notice: Subject to any disclaimer, the term of this patent is extended or adjusted under 35 U.S.C. 154(b) by 82 days.

(21) Appl. No.: 13/293,697

(22) Filed: Nov. 10, 2011

(65) Prior Publication Data

US 2012/0114587 A1 May 10, 2012

Related U.S. Application Data

(60) Provisional application No. 61/412,186, filed on Nov. 10, 2010.

(51) Int. Cl.
*A61L 9/04* (2006.01)

(52) U.S. Cl.
USPC ............................ 422/123; 422/120; 261/78.2

(58) Field of Classification Search
USPC ......................... 422/4, 5, 120, 123; 261/78.2
See application file for complete search history.

(56) References Cited

U.S. PATENT DOCUMENTS

| | | | |
|---|---|---|---|
| 3,097,645 A * | 7/1963 | Lester | 128/200.21 |
| 3,442,602 A | 5/1969 | Diehl | |
| 4,070,423 A * | 1/1978 | Pierce | 261/77 |
| 5,861,096 A | 1/1999 | Mason et al. | |
| 5,989,497 A | 11/1999 | Labonte, Jr. | |
| 6,770,247 B1 | 8/2004 | Romack et al. | |
| 2006/0120913 A1 | 6/2006 | Wuest | |
| 2008/0019862 A1 | 1/2008 | White | |
| 2010/0143204 A1 | 6/2010 | Ortiz et al. | |

* cited by examiner

*Primary Examiner* — Sean E Conley
(74) *Attorney, Agent, or Firm* — Martin & Ferraro, LLP

(57) ABSTRACT

A system for producing a deodorizing or odor neutralizing fog includes a tank with an input port and an exit port, and a fogging portion located within the tank. A deodorizing or odor neutralizing liquid is added to the tank upon which the fogging portion is configured to float. Compressed air is input through said input port and is expelled on the deodorizing or odor neutralizing liquid through at least one nozzle located on the fogging portion, thereby vaporizing the deodorizing or odor neutralizing liquid. The vapor combines with the compressed air within the tank to form the deodorizing or odor neutralizing fog.

10 Claims, 5 Drawing Sheets

DEODORIZING SYSTEM AND METHOD FOR USE THEREOF

RELATED APPLICATION

The present application claims the benefit of U.S. Provisional Patent Application Ser. No. 61/412,186, filed Nov. 10, 2010; the entire contents of which is incorporated herein by reference.

BACKGROUND OF THE INVENTION

1. Field of the Invention

By their very nature, landfills, sewer systems, and certain other industrial and agricultural sites generate offensive odors. Accordingly, when proximate to residential and/or commercial areas, the odor is at the very least a nuisance and sometimes can be unbearable to occupants of the residential and/or commercial areas. As such, deodorizing systems have been employed to mask or neutralize the offensive odors from such sites.

2. Description of the Related Art

Deodorizing systems typically release deodorizing or neutralizing liquid suspended in air or mixed with water and sprayed into the air to combat the offensive odors. These systems, however, typically release heavy droplets of the deodorizing or neutralizing liquid relative to the amount necessary to perform the desired function. Heavy droplets by their nature will readily fall to the ground in comparison to lighter droplets of the liquid. Quality deodorizing or neutralizing liquid can cost as much as $100 per gallon and typical deodorizing systems available on the market can use 12 gallons per system per 8 hour shift. Many landfills will have multiple systems operating at various locations around the landfill 24 hours a day. Therefore, there is a need for a deodorizing system which minimizes the deodorizing or neutralizing liquid utilized while still providing an acceptable masking or neutralizing of the odors. In particular, such a system for minimizing the liquid used preferably utilizes a fog containing the deodorizing or neutralizing liquid finely suspended in air. As such, the fog formed from the deodorizing or neutralizing liquid preferably contains smaller droplets of liquid suspended in the air delivered to the surrounding area relative to currently available systems.

SUMMARY OF THE INVENTION

The present invention in one preferred embodiment is drawn to a deodorizing system configured to produce a deodorizing or neutralizing fog to be distributed to mask or neutralize an offensive odor and a method for use thereof. The deodorizing system is configured to vaporize a deodorizing or neutralizing liquid by expelling high pressure air on or under the surface thereof. The vaporized liquid is mixed with compressed air in a tank to generate a deodorizing or neutralizing fog. The fog is then released from the tank through a series of tubes and nozzles to distribute the fog over the area from which the offensive odor is emanating.

It is to be understood that both the foregoing general description and the following detailed description are exemplary and exemplary only and are not restrictive of the invention, as claimed.

BRIEF DESCRIPTION OF THE FIGURES

The accompanying drawings, which are incorporated in and constitute a part of the specification, illustrate preferred embodiments of the invention. Together with the description, they serve to explain the objects, advantages and principles of the invention. In the drawings.

DETAILED DESCRIPTION OF THE PREFERRED EMBODIMENT

Figure 1:
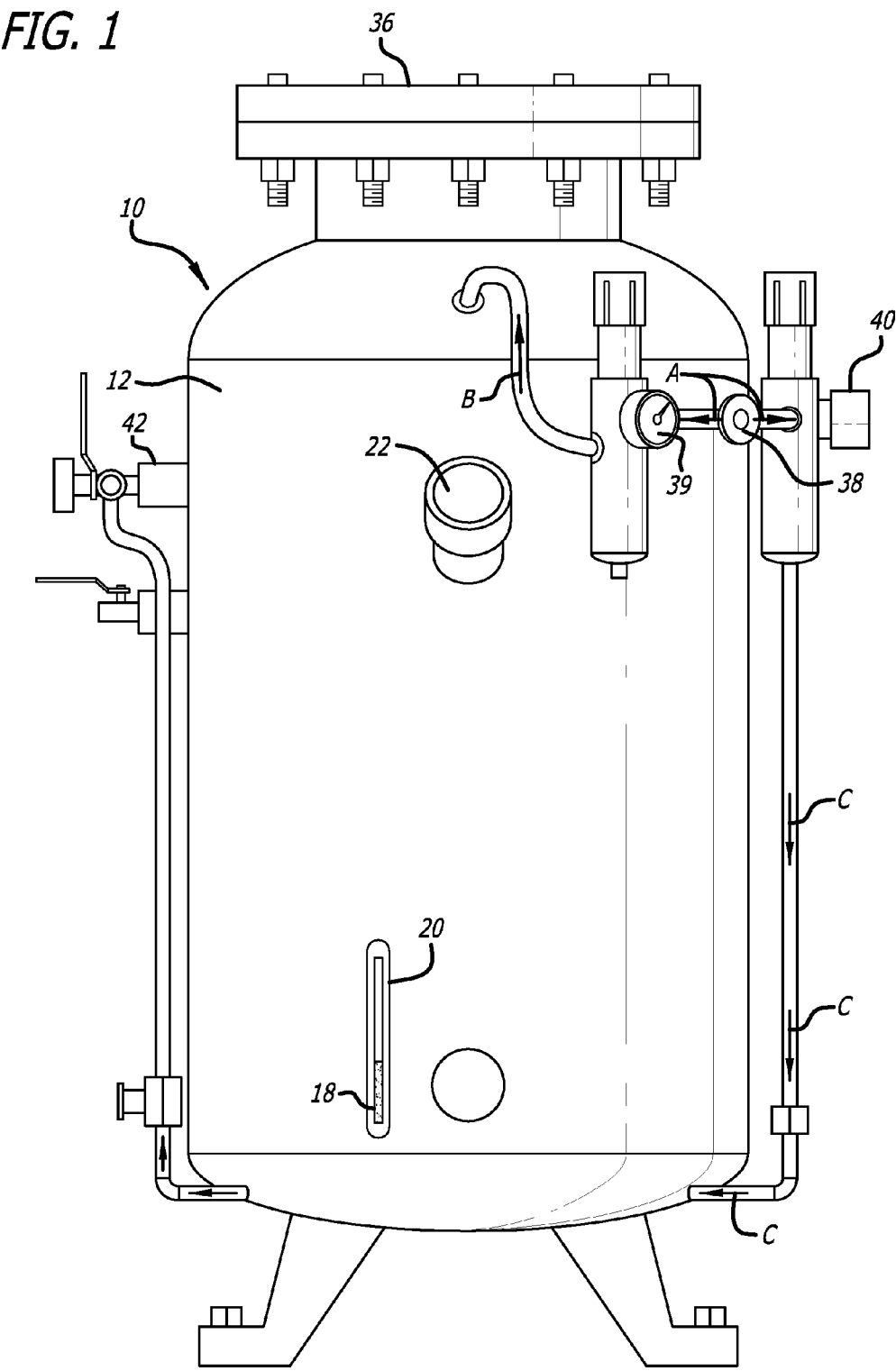
FIG. 1 is a front elevation view of a deodorizing system according to the present invention.

A deodorizing system according to the present invention is generally indicated by the numeral 10 in the accompanying drawings. System 10 includes a tank 12 and a fogging portion 14 (shown in FIGS. 3 and 4) included in an interior 16 of tank 12. Tank 12 is configured to contain a certain level of deodorizing or neutralizing liquid as indicated by liquid 18 visible in a sight glass of a fill gauge 20 shown in FIG. 1. As discussed below, liquid 18 is ultimately suspended in a deodorizing fog released by system 10.

Figure 2:
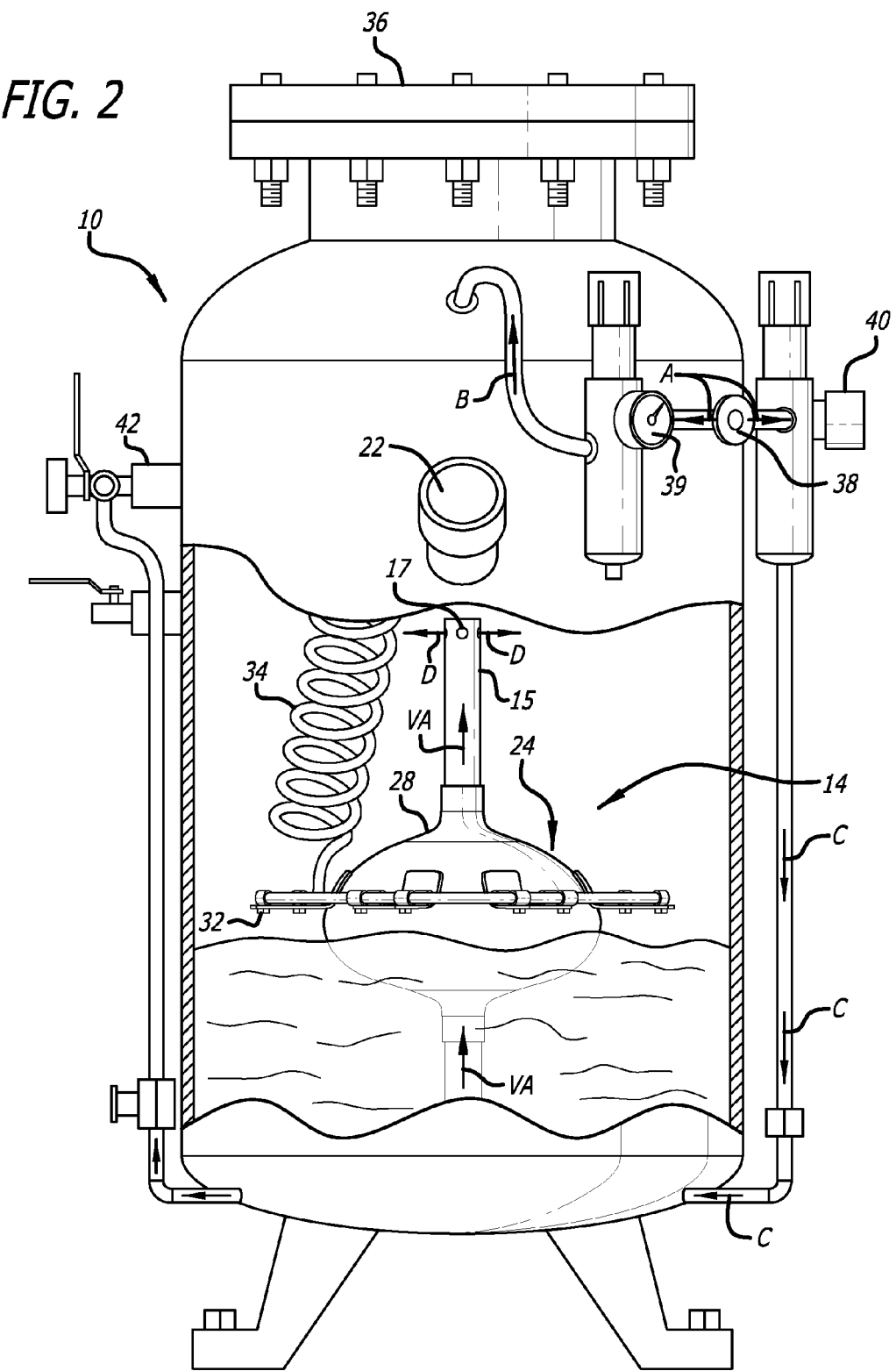
FIG. 2 is a front elevation view of the deodorizing system depicted in FIG. 1 with a portion of the tank removed to expose the interior thereof.
Figure 3:
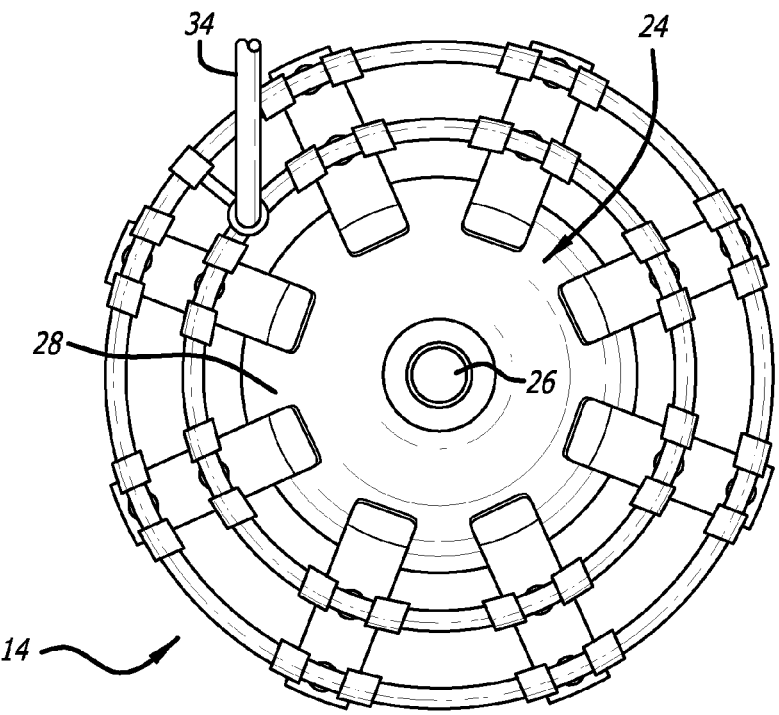
FIG. 3 is a top view of a fogging portion of the deodorizing system.
Figure 4:
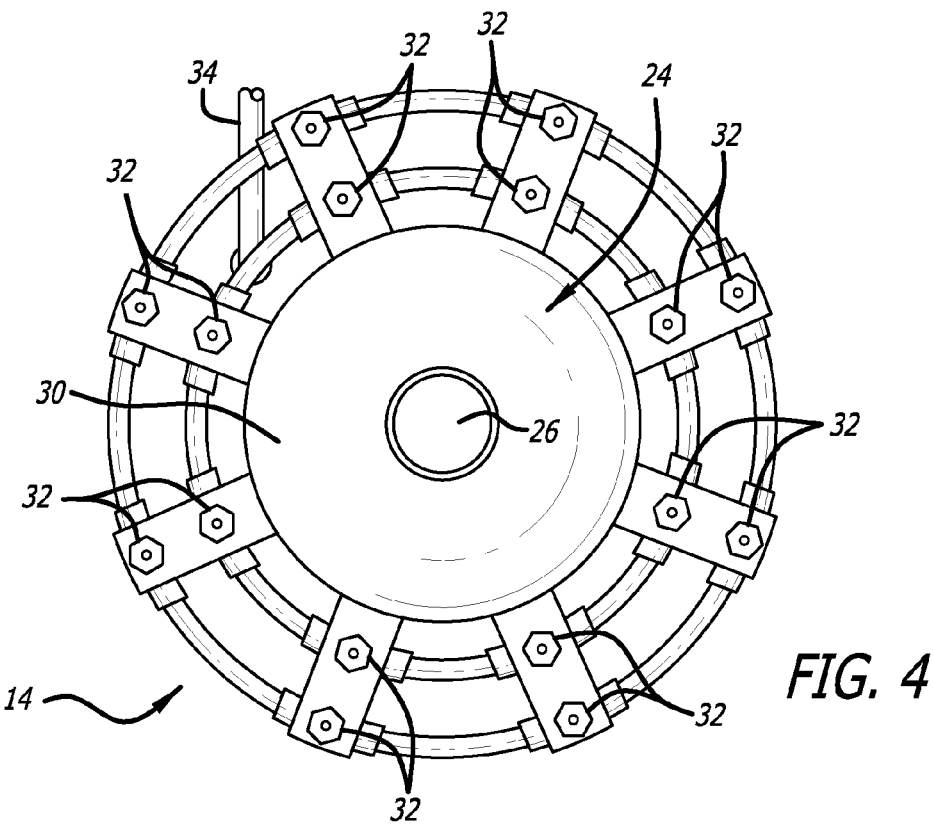
FIG. 4 is a bottom view of the fogging portion depicted in FIG. 3.
Figure 5:
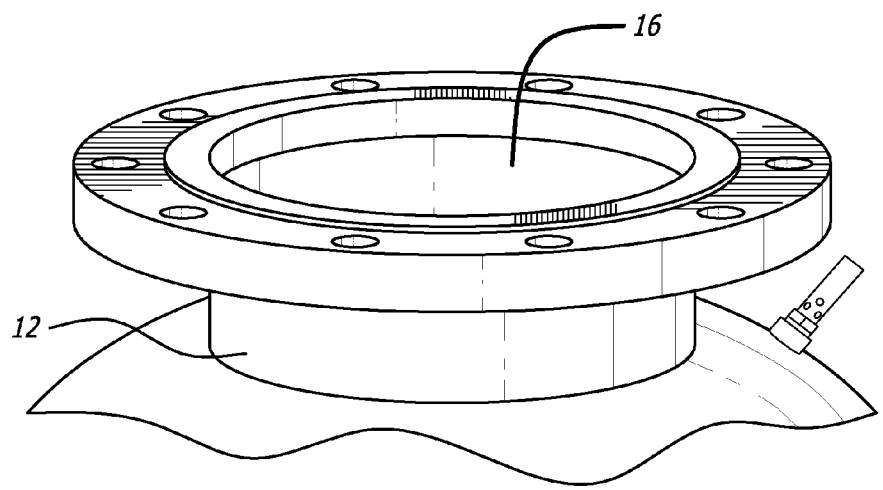
FIG. 5 is a perspective view of a top portion of the tank of the deodorizing system depicted in FIG. 1.

Fogging portion 14 of system 10 includes a tube 15 extending upwardly through interior 16 of tank 12. As shown in FIG. 2, tube 15 extends from the bottom center of tank 12 to just below a fill cap 22 used to pour liquid 18 into system 10. Furthermore, a float 24 rides upwardly and downwardly with respect to tube 15. As depicted in FIGS. 2-4, float 24 has a generally spherical shape with an opening 26 therethrough. Alternatively, float 24 may have a toroidal shape. When tube 15 is received through opening 26, float 24 and fogging portion 14 are configured to float on top of liquid 18 contained in tank 12. As the level of liquid 18 changes, float 24 and fogging portion 14 move upwardly or downwardly with respect to the tube.

The float 24 includes an upper surface 28 (shown in FIG. 3) and a lower surface 30 (shown in FIG. 4). As depicted in FIG. 4, various nozzles 32 are provided surrounding float 24 and oriented in the same general direction as lower surface 30. Nozzles 32 are configured to expel compressed air on (or under) the surface of liquid 18, and can be arranged to maximize impact of the compressed air on liquid 18. In one preferred embodiment, nozzles 32 are arranged to float approximately 1 to 1½ inches above liquid 18 to produce the fog. In another embodiment, nozzles 32 are submerged below the surface of liquid 18. The optimum nozzle orientation relative to the surface of liquid 18 will depend on the specific liquid being employed, the tendency of the specific liquid to foam, and the fogging capabilities of the specific liquid when high pressure air is directed at the surface or just below the surface thereof. In one preferred embodiment, as depicted in FIG. 4, nozzles 32 can be arranged ire two concentric rings. Nozzles 32 are connected by tubing 34 to a compressed air source (not shown).

The impact of the compressed air on liquid 18 creates the fog. That is, the impact of the compressed air vaporizes liquid 18 by creating tiny droplets thereof, and mixing the tiny droplets of liquid 18 with the compressed air creates the deodorizing fog. Tank 12 has a lid 38 to contain the fog and pressurize tank 12 to facilitate the movement of the fog out of tank 12 via exit port 42 and along hoses to nozzles (not shown) for distribution over a wide area.

As best seen in FIGS. 1 and 2, input port 38 is adapted to receive a source of compressed air. The air moves through input port 38 and follows arrows A into gauges 39 and 40. Gauge 39 indicates the air pressure leading into tank 12 along arrow B through tubing 34 and nozzles 32. Gauge 40 indicates the air pressure leading down to the bottom of tank 12 along arrows C and into the lower portion of upwardly extending tube 15 upon which float 24 slides. The air traverses tube 15 (indicated by vertical arrows VA) and preferably exits tube 15 via holes 17 on the side of tube 15 (indicated by arrows D) at a level which is preferably below an exit port 42. One advantage to having side holes 17 in tube 15 below the height of exit port 42 is to aid in keeping foam from exiting exit port 42 under situations were the interaction of the high pressure air against liquid 18 causes foam in addition to fog. The air flowing from side holes 17 of tube 15 acts to deter the foam from rising above holes 17 in tube 15. In alternative embodiments, air can exit from tube 15 at multiple locations along the length of tube 15 above the surface of liquid 18.

One preferred embodiment of the present invention includes an 80 gallon tank 12 and approximately 20 PSI greater air pressure flowing to nozzles 32 of fogging portion 14 than through tube 15. Interior 16 of tank 12 is preferably stainless steal or aluminum or otherwise consists of corrosion resistant material due to the corrosive properties of many deodorizing and neutralizing liquids. In a preferred embodiment, the air pressure to nozzles 32 of fogging portion 14 is 100 PSI and to tube 15 upon which fogging portion 14 slides is 80 PSI. In this embodiment, side holes 17 in tube 15 are ⅛ inch in diameter and 8 in number circling tube 15. A preferred nozzle 32 includes a fan-shaped configuration.

Exit lines (not shown) attached to valves 52, which are attached to opposite sides of exit port 42, can be provided adjacent the perimeter of, for example, a landfill to disperse the deodorizing fog. The exit lines, by way of example, may each be 250 feet long and have nozzles spaced every 10 feet along the exit lines to disperse the fog under pressure. The tiny drops mixed with the air to form the deodorizing fog can be dispersed over a large swath of area to counteract the odor emanating from the landfill.

Figure 6:
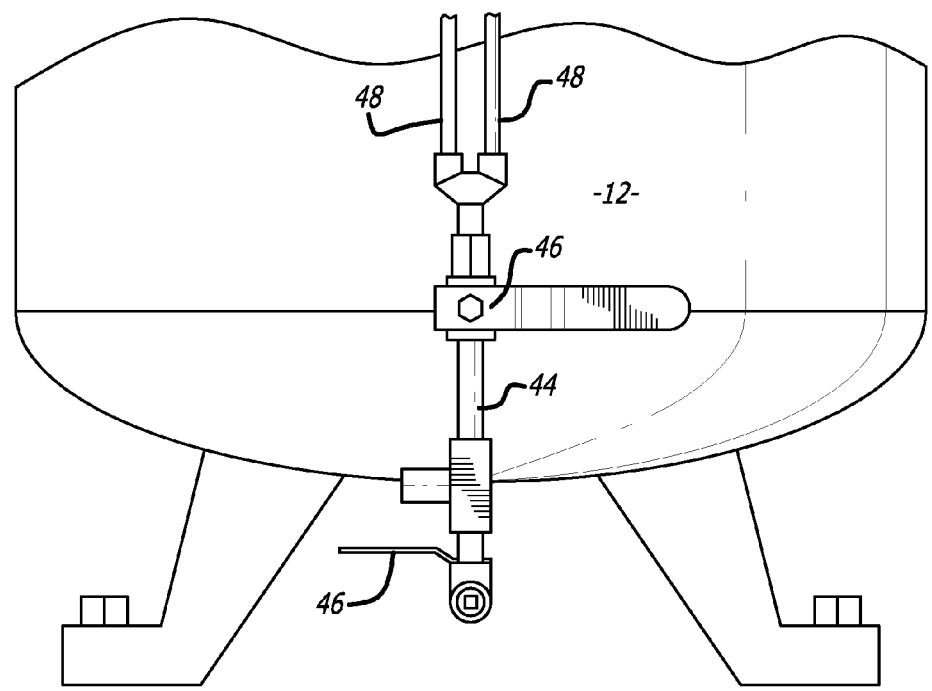
FIG. 6 is a left side elevation view of a bottom portion of the tank of the deodorizing system depicted in FIG. 1.
Figure 7:
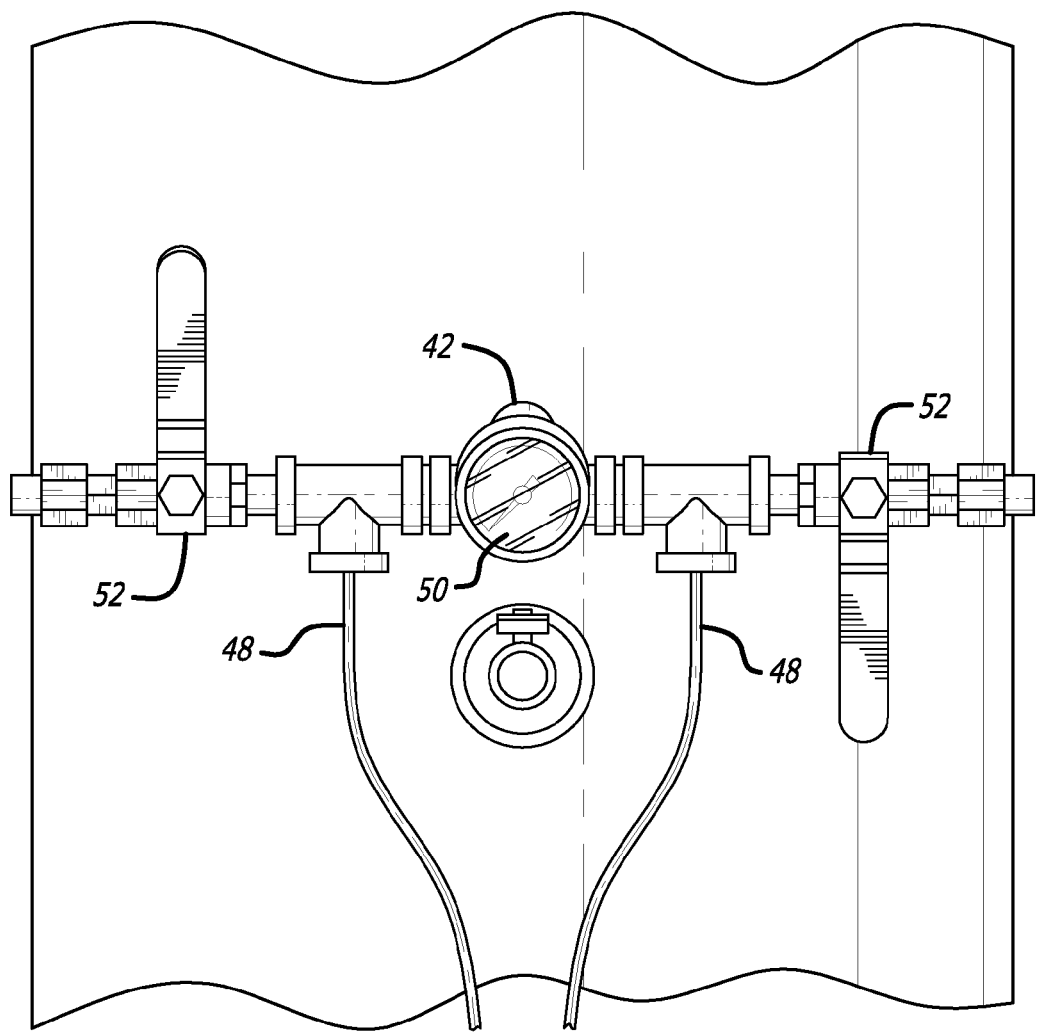
FIG. 7 is a left side elevation view of a middle portion of the tank of the deodorizing system depicted in FIG. 1.

While system 10 and the method for use thereof described above has focused on using a fog of liquid 18 generated under high pressure within tank 12 with additional pressure striking liquid 18, under certain circumstances additional deodorizing or neutralizing liquid may be desired beyond that created by fogging portion 14 of system 10. When odor is particularly strong, present system 10 permits the introduction of liquid 18 directly into the pressurized lines containing the fog proximate exit port 42. As best shown in FIG. 6, an auxiliary product injection line 44 leads from the bottom of tank 12 and liquid 18 is permitted to flow through injection line 44 upon opening of valves 46. Injection line 44 divides into lines 48 to allow liquid 18 to be introduced to each side of exit port 42, as best shown in FIG. 7. Gauge 50 indicates the air pressure exiting tank 12.

For purposes of transporting system 10 to a desired location for operation, a preferred embodiment includes a skid configuration beneath tank 12 to receive forks from a fork lift and a heavy D-ring of lid 36 to receive a chain for lifting system 10 via a dozer or other heavy equipment.

What is claimed is:

1. A system for producing a deodorizing or odor neutralizing fog, said system comprising:
   a tank configured to contain a deodorizing or neutralizing liquid therein, said tank having an input port and an exit port, said input port being configured to allow for the input of compressed air, said exit port being configured to allow for the exit of the deodorizing or odor neutralizing fog; and
   a fogging portion having an upper surface and a lower surface, said fogging portion being located within said tank and being configured to float on top of the deodorizing or neutralizing liquid, said fogging portion having at least one nozzle oriented at least in part toward the deodorizing or neutralizing liquid, said at least one nozzle being configured to expel compressed air on the deodorizing or neutralizing liquid.

2. The system of claim 1, further comprising a hollow tube extending upwardly through an interior of said tank.

3. The system of claim 2, wherein said fogging portion includes a hole extending from said upper surface to said lower surface, said hole being configured to fit said tube therethrough and thereby allow said fogging portion to move up and down with respect to said tube.

4. The system of claim 3, further comprising a first pressure regulator configured to regulate the pressure of the compressed air expelled from said at least one nozzle.

5. The system of claim 4, further comprising a second pressure regulator configured to regulate the pressure of the compressed air entering the tank through said hollow tube.

6. The system of claim 5, wherein said hollow tube includes side holes proximate the top thereof.

7. The system of claim 6, further comprising exit lines, configured to disperse the deodorizing or odor neutralizing fog, said exit lines being attached to said exit port on said tank.

8. The system of claim 7, further comprising nozzles on said exit ones.

9. The system of claim 1, further comprising a base configured to allow movement of said system with a fork lift.

10. The system of claim 1, wherein said at least one nozzle is adjustable with respect to the distance between said nozzle and the surface of the deodorizing or odor neutralizing liquid.

\* \* \* \* \*

UNITED STATES PATENT AND TRADEMARK OFFICE
CERTIFICATE OF CORRECTION

PATENT NO.        : 8,562,914 B2                              Page 1 of 1
APPLICATION NO.   : 13/293697
DATED             : October 22, 2013
INVENTOR(S)       : John D. Slutz et al.

It is certified that error appears in the above-identified patent and that said Letters Patent is hereby corrected as shown below:

In the Claims

<u>Column 4, Claim 8</u>:
Line 47: change "ones" to -- lines --.

Signed and Sealed this
Eighteenth Day of February, 2014

Michelle K. Lee
*Deputy Director of the United States Patent and Trademark Office*